United States Patent [19]

Durham et al.

[11] Patent Number: 5,004,851

[45] Date of Patent: Apr. 2, 1991

[54] PROCESS TO PRODUCE AROMATICS OF LOW ACID-WASH COLOR

[75] Inventors: George R. Durham, Baton Rouge; Randy S. Hebert, Donaldsonville, both of La.

[73] Assignee: The Dow Chemical Company, Midland, Mich.

[21] Appl. No.: 275,665

[22] Filed: Nov. 22, 1988

Related U.S. Application Data

[63] Continuation of Ser. No. 98,837, Sep. 21, 1987, abandoned.

[51] Int. Cl.$^5$ .............................................. C07C 7/163
[52] U.S. Cl. .................................. 585/260; 585/258; 585/259; 585/261; 585/807
[58] Field of Search ............... 585/807, 258, 259, 260, 585/261, 262

[56] References Cited

FOREIGN PATENT DOCUMENTS

| | | | |
|---|---|---|---|
| 1508976 | 1/1968 | France | 585/807 |
| 977449 | 11/1982 | U.S.S.R. | 585/807 |
| 911208 | 3/1961 | United Kingdom | 585/807 |

*Primary Examiner*—Asok Pal

[57] ABSTRACT

Nitration Grade benzene is made from a benzene stream with impurities including olefins by first fractionally distilling the benzene to a purity of at least 99 mole percent and subsequently passing the stream in a liquid phase in the presence of hydrogen through a hydrogenation step with a palladium catalyst under conditions such that substantially all olefins remaining in the stream are hydrogenated to paraffins.

20 Claims, No Drawings

PROCESS TO PRODUCE AROMATICS OF LOW ACID-WASH COLOR

CROSS-REFERENCE TO RELATED APPLICATION

This is a continuation of application Ser. No. 098,837 filed Sept. 21, 1987, now abandoned.

BACKGROUND OF THE INVENTION

The present invention relates to the art of producing a purified grade of benzene.

Benzene is ordinarily purified by fractional distillation. Distillation, however, cannot remove certain unsaturated impurities such as diolefins which have a boiling point very close to that of benzene. Benzene which has only been fractionally distilled does not ordinarily have an acid-wash number of 2 or less.

Acid-wash color is a widely used measure of the level of unsaturated impurities in benzene. The test for acid-wash color is described in ASTM D-848-81. The test involves mixing sulfuric acid with benzene and shaking the mixture so that sulfuric acid will react with unsaturated impurities in the benzene. The discoloration caused by the product of sulfuric acid and the unsaturated impurities is the acid-wash color, which is measured and translated into a numerical assessment of discoloration. "Nitration Grade" benzene must have an acid-wash number of 2 or less.

Olefins have long been removed by passing the benzene through a clay treatment bed. The purification processes using clay treatment beds are described in several U.S. patents: Fukuda et al., *Production of High Purity Benzene from Cracked Petroleum Residues*, U.S. Pat. No. 3,400,168 (Sept. 3, 1968); Davis, *Purification of Aromatic Hydrocarbons*, U.S. Pat. No. 3,485,884 (Dec. 23, 1969); Ehrlich et al., *Hydrodealkylation*, U.S. Pat. No. 3,754,045 (Aug. 21, 1973); Vickers, *Aromatics Extraction and Distillation Process*, U.S. Pat. No. 4,070,408 (Jan. 24, 1978); and Takahashi et al., *Process for Producing High Purity Benzene*, U.S. Pat. No. 4,247,729 (Jan. 27, 1981). Clay beds are very inefficient from an industrial standpoint. They operate at high temperatures and high back pressures, are toxic hazards for persons exposed to the spent clay, and cannot be regenerated so that used clay must be landfilled in an environmentally sound manner.

Recent patents have also suggested that olefins can be removed by passing benzene over a hydrogenation catalyst with hydrogen prior to fractional distillation. In that manner, olefin impurities are hydrogenated to paraffins, which are easier to distill from the benzene. Patents which have discussed such a process include: Love et al., *Production of Hydrocarbon Solvents of Low Acid-Wash Color*, U.S. Pat. No. 2,731,506 (Jan. 17, 1956); Fukuda et al., *Process for Producing High Purity Benzene*, U.S. Pat. No. 3,310,592 (Apr. 19, 1965); Nelson et al., *Method for Improving the Quality of Dealkylated Aromatic Compounds*, U.S. Pat. No. 3,310,593 (Mar. 21, 1967); Peterson et al., *Method for Improving the Quality of Aromatic Compounds*, U.S. Pat. No. 3,310,594 (Mar. 21, 1967); Horne et al., *Benzene from Pyrolysis Gasoline*, U.S. Pat. No. 3,625,879 (Dec. 7, 1971); Eisenlohr et al., *Production of Extra Pure Aromatics*, U.S. Pat. No. 3,869,377 (Mar. 4, 1975); and Derrien et al., *Process for Producing Benzene by Hydrodealkylation of a Hydrocarbon Fraction Comprising Alkyl-Aromatic Hydrocarbons, Olefinic Hydrocarbons and Sulfur Compounds*, U.S. Pat. No. 4,463,206 (July 31, 1984). Foreign sources which describe catalytic hydrogenation to purify aromatic materials include: Essler, East German Patent No. 129,269 (published Jan. 11, 1978); Sumitomo Chemical, Japanese Patent No. 52/136,205 (published Nov. 14, 1977); and Mitsui Toatsu Chemical, Inc., Japanese Patent No. 60/185,733-A (published Sept. 21, 1985).

Those processes may effectively remove olefin impurities from benzene. However, other impurities found in the benzene can deactivate the catalyst, necessitating frequent replacement of the catalyst. Furthermore, such processes may be wasteful of energy. The benzene must ordinarily be heated up to a temperature appropriate for a gas-phase hydrogenation, then cooled back to a liquid phase to prepare for fractional distillation, and then heated and cooled again in the distillation process. What is needed is a process to purify benzene and drive its acid-wash color down to 2 or less without generating substantial amounts of environmentally hazardous by-products and without the need to repeatedly heat the benzene to a gas phase and then cool it to a liquid phase.

SUMMARY OF THE INVENTION

The present invention is a process to produce an aromatic liquid with an acid-wash color of two or less, wherein a stream comprising primarily a liquid aromatic compound with some impurities which include olefins is first fractionally distilled to a purity of at least about 99 percent by weight and is subsequently passed in a liquid phase over a hydrogenation catalyst with a sufficient amount of hydrogen and under conditions such that substantially all olefins in the stream are hydrogenated to paraffins, but little aromatic liquid is hydrogenated. Surprisingly, when an aromatic stream is fractionally distilled before hydrogenation rather than after, according to the process of the instant invention, the aromatic liquid produced is Nitration Grade, the hydrogenation catalyst is protected from deactivating impurities, and the process can be maintained in preferred embodiments without repeated heating and cooling of the aromatic stream.

DETAILED DESCRIPTION OF THE INVENTION

The liquid aromatic compound to be treated by the instant process may be benzene, toluene, or other aromatic compounds which must meet standards for Nitration Grade solvents. Preferably, the compound to be purified by the present invention is benzene, and the stream which is to be treated according to the instant process comprises at least about 85 percent benzene by weight. More preferably, the stream comprises at least about 97 percent benzene. Preferably, the impurities in the benzene stream comprise toluene equal to about 2 to 14 percent of the whole stream and naphthalene, biphenyl, and olefin impurities equal to about 1 to 13 percent of the stream. Most preferably, the benzene stream is product from the hydrodealkylation of toluene or other alkyl-substituted aromatic compounds. Such processes are well known in the art and are described in Horne, *Benzene from Pyrolysis Gasoline*, U.S. Pat. No. 3,625,879 (Dec. 7, 1971) and Derrien et al., *Process for Producing Benzene by Hydrodealkylation of a Hydrocarbon Fraction Comprising Alkyl-Aromatic Hydrocarbons, Olefinic Hydrocarbons and Sulfur Compounds*, U.S. Pat. No. 4,463,206 (July 31, 1984).

Preferably, the aromatic stream is fractionally distilled in a two step process. First, the stream passes through a stabilization column to remove components lighter than the desired aromatic liquid. When the desired liquid is benzene, the temperature of benzene in the stabilization column is preferably at least about 100° C., more preferably at least about 115° C., and preferably at most about 160° C., more preferably at most about 145° C. Pressures in the column are preferably at least about 70 psig, more preferably at least about 115 psig, and preferably at most about 290 psig, more preferably at most about 220 psig. Light impurities in the benzene preferably come out overhead at about 100° C., whereas bottoms from the first step preferably come out at about 150° C. to 200° C. The composition of the bottoms is often little changed from that of the stream entering the first step, since light components are not a major part of the stream.

Second, the aromatic stream passes through a fractionating column, also known in the art as a finishing column, under conditions generally known in the art, in order to distill the aromatic liquid to a purity of 99+ percent. When the desired product is benzene, the bottoms from the stabilization column are cooled to preferably at least about 90° C., more preferably at least about 110° C., and preferably at most about 175° C., more preferably at most about 150° C. The maximum pressure in the column is preferably about 30 psig, more preferably about 14.5 psig. The minimum pressure in the column is preferably about 2.2.

The maximum temperature of aromatic compound which comes out of the column overhead is preferably about 120° C., more preferably about 90° C., and most preferably about 80° C. The minimum temperature is preferably about 20° C., more preferably about 55° C., and most preferably about 75° C. It is preferred that a condenser liquefy the aromatic compound and a reflux pump raise the pressure of the aromatic stream to 50 to 100 psig.

Preferably, part of the finished stream may be sent back to the finishing column for further reflux. Upon leaving the finishing column and going on to the third step, the aromatic liquid is preferably at least about 99 percent pure by weight and more preferably at least about 99.9 percent pure by weight, with olefins comprising a major impurity. Preferably, the acid-wash color of the aromatic liquid is no more than about 8, and more preferably no more than about 4.

The third step of the present invention comprises catalytically hydrogenating olefin impurities in the stream by passing the distilled stream admixed with hydrogen over a hydrogenation catalyst bed. Catalysts and the condition for their use are well known in the art. The catalyst preferably comprises palladium. Palladium on a metal oxide support is highly preferred. More preferably, the catalyst comprises 0.05 to 1 percent palladium. Most preferably, the catalyst comprises 0.05 to 0.5 percent palladium. The support is more preferably particulate alumina. The supported catalyst most preferably has a surface area of about 35 m² per gram.

The hydrogen may be pure hydrogen gas or hydrogen in an inert diluent such as methane. Preferably, the molar ratio of aromatic compound to hydrogen is between about 1:1.5 and about 1000:1, depending upon the amount of olefin in the aromatic stream. More preferably, the concentration of hydrogen in the hydrogenation step is enough to completely saturate all olefin impurities without leaving an unnecessary excess of hydrogen gas.

The aromatic stream may flow cocurrently or countercurrently with the hydrogen stream. The minimum pressure during hydrogenation is preferably about 30 psig. The maximum pressure during hydrogenation is preferably about 500 psig, and more preferably about 100 psig. Most preferably, the pressure is the pressure at which the aromatic stream leaves the reflux pump (about 50 to 100 psig).

The temperature of the catalytic hydrogenation step is preferably at least about 20° C. and more preferably at least about 40° C., preferably at most about 130° C. and more preferably at most about 90° C. Most preferably, the temperature of the hydrogenation step is approximately the temperature at which the aromatic stream comes off of the finishing column (described previously).

The hydrogenation takes place in a liquid-phase reaction, preferably with a residence time of at least 2 minutes. More preferably, the residence time is at most 40 minutes, and most preferably the residence time is at most 5 minutes. After leaving the catalytic hydrogenation step, the aromatic liquid passes through a flash drum, small column or other known means to remove excess hydrogen gas in order to prevent an explosion hazard in storage.

Benzene purified according to the present invention has an acid-wash color of less than 2, preferably less than 1, and is ready for storage and sale as "nitration grade" benzene without further refinement. The remaining impurities do not substantially affect the acid-wash number. In its preferred embodiments, the present purification process only requires that the benzene stream be heated once and utilizes the heat remaining in the stream thereafter. Furthermore, in the present process, impurities which are harmful to the catalyst are removed from the benzene stream upstream from the catalytic hydrogenation step, so that those impurities do not harm the catalyst.

ILLUSTRATIVE EXAMPLES

The following examples illustrate the proper functioning of the instant process, but are not intended to limit the scopes of either the specification or the claims.

EXAMPLE 1

A 6"×2' catalyst bed is prepared, using a catalyst of 0.3% palladium by weight on alumina (surface area approximately 35 m² per gram). A stream comprising 85% hydrogen and 15% methane by mole is passed over the catalyst at 80° C. for a few hours to ensure that the catalyst is fully reduced. When the catalyst is ready, distillation of the benzene stream begins and the hydrogen stream is left running.

First, effluent from a hydrodealkylation process for making benzene is cooled through heat exchangers to 60° C. at a pressure of 450 psig and passes through a flash drum where gaseous impurities are removed. Second, it enters a stabilization column at 130° C. and at a pressure of 175 psig. Third, bottoms from the stabilization column are cooled in a heat exchanger to 125° C. and pass into a finishing column at about 5 psig. Overheads are passed through a condenser and a reflux pump which liquefy the benzene and increase the pressure to 50 psig at a temperature of 55° C. About half of the overheads are sent back to the finishing column for further reflux and the rest proceed on to the catalyst bed.

Overheads proceeding to the catalyst bed are 99.93% benzene by mole and have an acid-wash color of about 4. They pass through the catalyst bed cocurrently with the hydrogen/methane stream over a residence time of 10.2 minutes. The molar ratio of benzene to hydrogen is 250:1. After leaving the catalyst bed, the benzene passes through a flash drum to remove excess hydrogen. The acid-wash color of the benzene is less than 1.

EXAMPLE 2

The same procedure as example 1 is followed, except that the temperature of benzene entering the catalyst bed is 100° C. and the pressure is 100 psig. The acid-wash color of the benzene produced is less than 1.

EXAMPLE 3

The same procedure as example 2 is followed, except that the residence time in the catalyst bed is 2.5 minutes. The acid-wash color of the benzene produced is less than 1.

EXAMPLE 4

The same procedure as Example 1 is followed, except that the benzene stream passes through the catalyst bed at a temperature of 100° C. for a residence time of 2.5 minutes. The acid-wash color of the benzene produced is less than 1.

EXAMPLE 5

The same procedure as Example 1 is followed, except that the molar ratio of benzene to hydrogen is 1000:1. The acid-wash color of the benzene produced is less than 1.

EXAMPLE 6

The same procedure as Example 5 is followed, except that the residence time of the benzene in the catalyst bed is 2.5 minutes. The acid-wash color of the benzene produced is less than 1.

EXAMPLE 7

The procedure of Example 1 is followed, except that the benzene passing into the catalyst bed has an acid-wash color of 8, a pressure of 40 psig, and a temperature of 25° C.; the benzene to hydrogen molar ratio is 0.83:1; and the benzene passes over the catalyst for a residence time of 10.2 minutes. The resulting benzene has an acid-wash color of less than 1.

EXAMPLE 8

The procedure of Example 1 is followed, except that the benzene passing into the catalyst bed has an acid-wash color of 8, a pressure of 155 psig, and a temperature of 44° C.; the hydrogen is a stream of 99+% by mole hydrogen and the benzene to hydrogen molar ratio is 1.67:1; and the benzene passes over the catalyst bed for 20 minutes. The resulting benzene has an acid-wash color of less than 1.

What is claimed is:

1. A process to produce benzene or toluene with an acid wash color of two or less from a stream containing primarily benzene or toluene with impurities which include olefins, said process comprising sequentially the steps of:
   (1) fractionally distilling said stream such that the purity of the benzene or toluene is increased to at least about 99 percent by weight; and
   (2) passing said stream after said distillation step in a liquid phase over a hydrogenation catalyst with a sufficient amount of hydrogen and under conditions such that substantially all olefins remaining in the stream are hydrogenated to paraffins but little benzene or toluene is hydrogenated.

2. The process of claim 1 wherein the catalyst comprises palladium on a metal oxide support.

3. The process of claim 2 wherein the catalyst comprises about 0.05 to about 1 percent palladium by weight on a metal oxide support, and the aromatic liquid is benzene.

4. The process of claim 3 wherein hydrogenation takes place at a temperature of 20° C. to 130° C. and a pressure of 30 to 100 psig.

5. The process of claim 4 wherein the benzene leaving the fractional distillation and going to the hydrogenation step is about 99.9 mole percent benzene or more.

6. The process of claim 5 wherein the hydrogenation step takes place at approximately the temperature at which the benzene leaves the fractional distillation step.

7. The process of claim 6 wherein the catalyst comprises about 0.05 to about 0.5 percent palladium by weight on alumina.

8. The process of claim 6 wherein the hydrogenation step takes place at a temperature of about 40° C. to about 90° C.

9. The process of claim 7 wherein the benzene leaving the hydrogenation step is "Nitration Grade" benzene without the need for further purification.

10. The process of claim 7 wherein the benzene leaving the hydrogenation step has an acid-wash number of about two or less.

11. The process of claim 10 wherein the benzene has an acid-wash number of about one or less.

12. The process of claim 1 wherein the stream comprising primarily benzene is effluent from a hydrodealkylation process.

13. The process consisting essentially of the steps set out in claim 1 followed by the step of:
   (3) removing hydrogen gas from the stream after said hydrogenation step by a means which leaves substantial paraffin impurities in the stream.

14. The process of claim 13 wherein the catalyst comprises palladium on a metal oxide support.

15. The process of claim 14 wherein hydrogenation takes place at a temperature of 20° C. to 130° C. and a pressure of 30 to 100 psig.

16. The process of claim 15 wherein the stream prior to processing comprises primarily benzene, the stream following removal of the hydrogen gas is a Nitration Grade benzene, and the stream leaving the fractional distillation and going to the hydrogenation step is about 99.9 mole percent benzene or more.

17. The process of claim 16 wherein the hydrogenation step takes place at approximately the temperature at which the benzene leaves the fractional distillation step.

18. The process of claim 17 wherein the catalyst comprises about 0.05 to about 0.5 percent palladium by weight on alumina.

19. The process of claim 18 wherein the benzene following removal of the hydrogen gas has an acid-wash number of about one or less.

20. The process of claim 13 wherein the stream comprising primarily benzene is effluent from a hydrodealkylation process.

* * * * *